United States Patent [19]

Tryggvason et al.

[11] Patent Number: 5,114,840
[45] Date of Patent: May 19, 1992

[54] METHOD FOR DETERMINING THE NUCLEOTIDE SEQUENCE OF A NOVEL α5(IV) CHAIN OF HUMAN TYPE IV COLLAGEN

[76] Inventors: Karl Tryggvason, Fyysikontie 8; Sirkka L. Hostikka, Tapionte 9 A 21, both of SK-90570 Oulu, Finland

[21] Appl. No.: 377,238

[22] Filed: Jul. 7, 1989

[51] Int. Cl.$^5$ .................. C12Q 1/68; C12P 19/34; C12N 1/06; C07H 15/12
[52] U.S. Cl. ......................... 435/6; 435/91; 435/172.3; 435/240.1; 435/252.3; 435/252.33; 435/259; 435/320.1; 536/26; 536/27; 536/28; 536/29; 935/9; 935/55; 935/56; 935/58; 935/73; 935/23; 935/24; 935/29; 935/31
[58] Field of Search ............... 435/6, 91, 172.3, 240.1, 435/252.3, 252.33, 259, 320; 536/26, 27, 28, 29; 935/9, 55, 56, 58, 73, 23, 24, 29, 31

[56] References Cited

PUBLICATIONS

"Complete primary structure of the alpha-1 chain of human basement membrane (type IV) collagen" by Soininen, et al., FEBS Letters, vol. 225, No. 1, 2, pp. 188-194, Dec. 1987.
"The Complete Primary Structure of the alpha-2 chain of Human Type IV Collagen and Comparison with the alpha-1 (IV) Chain" by Hostikka, et al., Journal of Biological Chemistry, vol. 263, No. 36, pp.19488-19493, Dec. 1988.
"Mapping of Alport Syndrome to the Long Arm of the X Chromosome" by Atkin, et al., Am. J. Human. Genet., 42, pp. 249-255, 1988.
"Localization of the Gene for Classic Alport Syndrome" by Flinter, et al., Genomics, 4, pp. 335-338, 1989.
"Alport Familial Nephritis" by Kieppei, et al., J. Clin. Invest., vol. 80, pp. 263-266, Jul. 1987.
"Localization of the Goodpasture Epitope to a Noel Chain of Basement Membrane Collagen" by Butkowski, et al., J. Biol. Chem., vol. 262, pp. 7874-7877, 1987.
"Structure and biological activity of basement membrane proteins", Max Planck-Institut fur Biochemic, Martrtinsried, vol. 180, pp. 487-502, 1989.

*Primary Examiner*—Robert A. Wax
*Assistant Examiner*—Stephanie N. Zitomer
*Attorney, Agent, or Firm*—Fay, Sharpe, Beall, Fagan, Minnich & McKee

[57] ABSTRACT

The present invention provides for a method for isolating and partially characterizing the nucleotide sequence for a novel polypeptide chain of human basement membrane (type IV) collagen, referred to as the α5(IV) polypeptide chain. The invention provides for the use of the identified nucleotide sequence (or DNA fragments thereof) to detect mutations in individual genes specific for the α5(IV) chain which can, directly or indirectly, produce several human diseases. Moreover, the invention also relates to procedures for determining genetic or acquired disorders of basement membranes using the identified nucleotide sequence (or DNA fragments thereof) of the α5(IV) polypeptide chain, probes specific to DNA fragments of said nucleotide sequence, or antibodies to the nucleotide sequence or DNA parts thereof. Also, the invention relates to the use of gene fragments generated through amplification from human genomic or cloned DNA for detection and analysis of the gene, such as in detection of mutations.

27 Claims, 6 Drawing Sheets

Collagenous domain | NC-domain

```
G L X G K P G D T G P P A A G A V M R G F V F T R H Y Q    Bovine α3 (IV)
            G P P G F G P G Y L S G F L L V L               Bovine α4 (IV)
G P D G L Q G P P P G P P G T S S V A H G F L T I R H S Q    Human α5 (IV)
```

METHOD FOR DETERMINING THE NUCLEOTIDE SEQUENCE OF A NOVEL α5(IV) CHAIN OF HUMAN TYPE IV COLLAGEN

FIELD OF THE INVENTION

The present invention relates to a method for isolating and identifying the nucleotide sequence of a novel polypeptide chain, termed α5(IV), of human type IV collagen, the major structural component of basement membranes. In addition, the present invention is also directed to the isolated and purified polypeptide chain encoded by the nucleotide sequence of the invention.

BACKGROUND OF THE PRIOR ART

Basement membranes are a highly specialized part of the extracellular matrix and they form the thin sheets that separate the cells of organ tissues from the fibrillar connective tissues. The basement membranes form a substratum for orderly growing cells in the body and they play an important role in cell differentiation during the formation of organs in the developing embryo. In addition, they also play a key role in the correct regeneration of tissues following injuries such as during post-wound reformation of skin and growth of nerves.

Furthermore, the basement membranes also have crucial special functions, such as in the filtration of macromolecules in kidney and blood vessels. This is best exemplified by the renal glomerular basement membrane where the filtration of blood results in the formation of primary urine that is devoid of cells and large macromolecules (proteins).

The basement membranes are composed of several proteins, many of which are found only in the membranes. Type IV collagen is the major structural component but other specific protein components include laminin, entactin (nidogen) and a heparin sulfate proteoglycan. Additionally, the basement membranes may contain fibronectin and type VII collagen that are also present in other tissues. The differences in the molecular composition of basement membrane in different tissues is not well known but a protein called pemphigoid antigen is probably only present in the basement membrane of skin. It is currently thought that there exists a number of other proteins that are specific for certain basement membranes.

Type IV collagen is the predominant structural component of basement membranes and it can provide up to 60% of the structure. As it is true for collagens in general, type IV collagen molecules are composed of three α chains that are coiled around each other to form a rod-like triple helical molecule that is about 1.5 nm in diameter and about 400 nm in length. At the carboxy terminal end the molecule has a large globular noncollagenous domain, called NC-domain, that has a diameter of about 15 nm. Single type IV collagen molecules are linked with each other into a complex, flexible network-like structure (Timpl, Eur.J.Biochem., 180, 487–502, 1989) into which other basement membrane components are bound.

It was previously thought that the major form of type IV collagen was composed of two kinds of chains, α1-(IV) and α2(IV), with the molecular formula [α1(IV)-]₂α2(IV). Along this line, the applicants have determined the complete amino acid sequence of both the human α1(IV) and the α2(IV) chains from cloned cDNA molecules (Soininen, et al., FEBS Lett., 225, 188–194, 1987; Hostikka and Tryggvason, J.Biol.-Chem., 263, 19488–19493, 1988). The results showed that the α1(IV) chain contains 1,642 amino acid residues as compared with 1,676 residues for the α2(IV) chain. The carboxy terminal NC-domains of both chains are very similar with 63% identical amino acid residues. The sequence homology of the two chains in the triple helical region is considerably less or 49%.

However, recently the existence of two additional α chains, termed α3(IV) and α4(IV) have also been reported to be present in the basement membrane of lens (Butkowski, et al., J.Biol.Chem., 262, 7874–7877, 1987). Therefore, the currently available data indicates that there are type IV collagen molecules with varying chain compositions and the different forms may contribute to functional differences of the basement membrane in various tissues The applicants' present discovery of a new type IV collagen α chain, termed α5(IV), demonstrates that type IV collagen composition and therefore the whole basement membrane matrix is even more complex than was previously thought.

Due to the wide distribution of basement membranes in the body, they are frequently affected in local and systemic diseases and in many instances, the consequent pathological changes lead to severe clinical complications. These disease may be both genetically determined inherited diseases that are due to gene mutations leading to an abnormal function of the basement membrane or they can be acquired, i.e. complications of diseases that do not primarily involve the basement membrane. Examples of inherited diseases are: (1) the congenital nephrotic syndrome that is characterized by extensive leak of blood proteins through the renal glomerular basement membrane into urine (proteinuria); and, (2) the Alport's syndrome where malfunction of the basement membranes leads to the passage of blood cells into urine (hematuria), eye lesions and hearing loss. The actual gene defects leading to the congenital nephrotic syndrome or the Alport's syndrome are yet completely unknown. Both diseases are lethal but they may be treated with kidney transplantation.

The best known example of an acquired basement membrane disease is diabetes mellitus where the basement membrane structure is affected in almost all tissues of the body resulting in dysfunction of small blood vessels (microangiopathy), kidneys (nephropathy), and nerves (neuropathy). The biochemical alterations leading to these malfunctions are still poorly understood.

The present invention, directed to a process for isolating and identifying the nucleotide sequence of a new polypeptide chain of human type IV collagen (i.e. α5-(IV)), is of important significance in the diagnosis of basement membrane disorders. In this regard, genetic mutations leading to the abnormal function of the basement membrane can be detected in the DNA of affected individuals by comparing the nucleotide sequences, etc.

SUMMARY OF THE INVENTION

The present invention provides for a method for isolating and partially characterizing the nucleotide sequence of a novel polypeptide chain of human basement membrane (type IV) collagen, referred to as the α5(IV) polypeptide chain. The invention provides for the use of the identified nucleotide sequence (or DNA fragments thereof) to detect mutations in individual genes specific for the α5(IV) chain which can, directly or indirectly, produce several human diseases. Moreover, the invention also relates to procedures for determining genetic or acquired disorders of basement membranes using the identified nucleotide sequence (or DNA fragments thereof) of the α5(IV) polypeptide chain, probes specific to DNA fragments of said nucleotide sequence, or antibodies to the nucleotide sequence or DNA parts thereof. Also, the invention relates to the use of gene fragments generated through amplification from human genomic or cloned DNA for detection and analysis of the gene, such as in detections of mutations.

The invention also provides for the use of the identified nucleotide sequence (or DNA fragments thereof) to measure the transcriptional activity of the genes that lead to the synthesis of messenger RNA specific for α5(IV). The invention further provides for the use of the genes or their sequence information to synthesize the α5(IV) protein itself or fragments thereof. Along this line, the invention relates to the use of the identified nucleotide sequence (or DNA parts thereof) to synthesize the α5(IV) chain or modifications of this protein by inserting genes into microorganisms or other hosts which use the gene to synthesize the protein. Additionally, the invention relates to the use of the identified nucleotide sequence (or DNA parts thereof) to correct for genetic defects leading to human diseases involving basement membranes with a defective α5(IV) protein.

Furthermore, the present invention involves several different embodiments. The invention provides cDNA clones coding for part of the α5(IV) chain of human type IV collagen. The invention is directed in particular to three cDNA clones (i.e. PL31, MD6 and M19) of the identified nucleotide sequence. In addition, the invention also provides for a nucleotide sequence which encodes an amino acid sequence of the α5(IV) chain of type IV collagen.

The invention further provides for recombinant DNA cloning vectors and transformed hosts which contain a vector which has a cDNA insert which codes for the human α5(IV) chain.

BRIEF DESCRIPTION OF THE DRAWINGS

The following is a brief description of the drawings which are presented for the purpose of illustrating the invention and not for the purpose of limiting same.

FIG. 2 (A and B) shows the coding nucleotide sequence (first line) of the cDNA clones and the derived amino acid sequence (second line) providing a part of the sequence for the human α5(IV) polypeptide chain of type IV collagen. The interruptions in the Gly-X-Y repeat sequence are shown by boxes and the cysteine residues that are all conserved in the NC-domain are encircled. The nucleotide sequence of the oligonucleotide probe coding for the Cys-Gln-Val-Cys-Met amino acid sequence is underlined.

FIG. 3 (A and B) shows alignment of the cDNA derived amino acid sequence of the novel α5(IV) polypeptide chain with corresponding region of the human α1(IV) and α2(IV) chains previously determined by the applicants.

FIG. 4 shows the alignment of a part of the sequence for the α5(IV) polypeptide chain with the corresponding reported sequences of the bovine α3(IV) and α4(IV) chains of type IV collagen.

BROAD DESCRIPTION OF ASPECTS OF THE INVENTION

Figure 1:
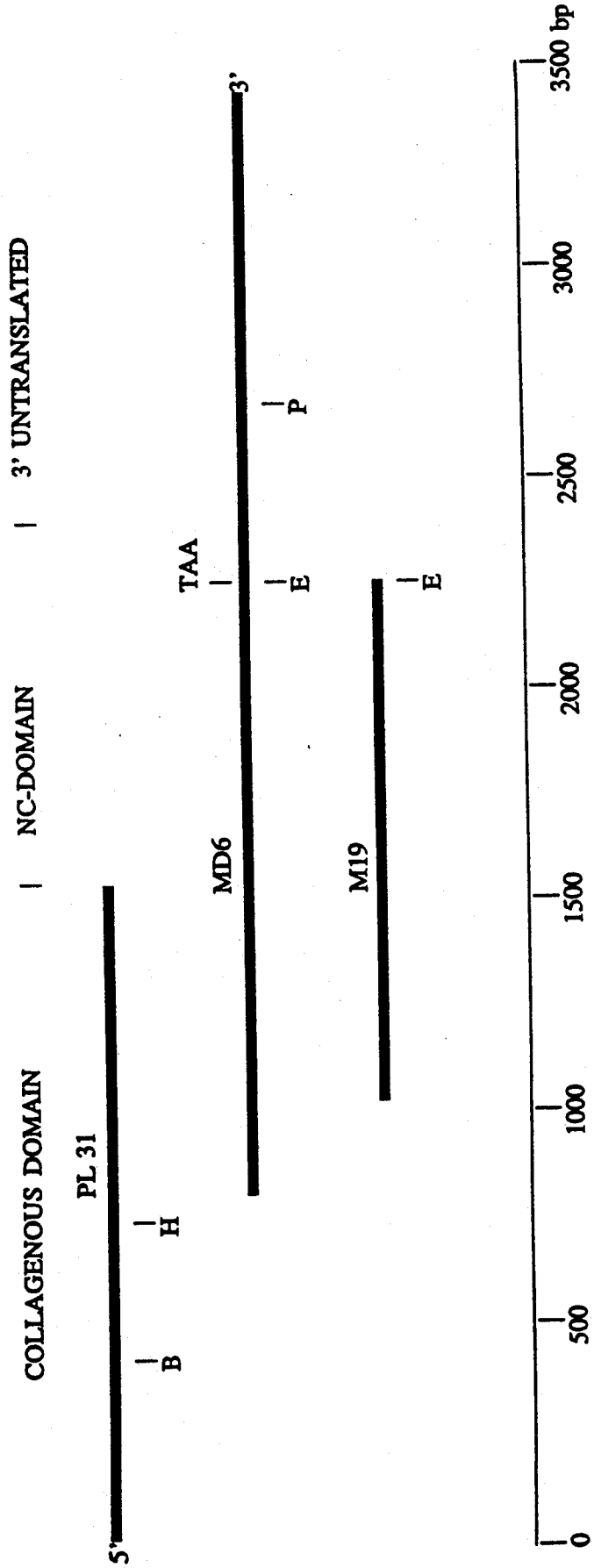
FIG. 1 is a restriction map of the three cloned cDNAs (i.e. PL31, MD6, and M19) that code for the novel α5(IV) polypeptide chain of type IV collagen. A scale demonstrating the size differences in base pairs is shown below the cloned cDNAs. The regions coding for the carboxy terminal end NC-domain of the protein as well as the part of the collagenous domain is indicated. Restriction endonuclease cleavage sites BamHI(B), EcoRI(E), HindII(H), and PstI(P) are also shown.

Proteins are the molecules that determine the structure and function of living organisms. The protein molecules are formed from over 20 different kinds of amino acids that are bound to each other in chain like structures (polypeptide chains). Depending on the amino acid sequence, the proteins can fold in a variety of ways, each protein having a distinct amino acid sequence, form, and function. The amino acid sequence is predetermined in the information contained in the DNA sequence of the corresponding gene. This DNA sequence, in turn, consists of a linear array of four bases, adenine (A), guanine (G), thymine (T), and cytosine (C). Mutations, i.e. changes in the DNA sequence of a gene, can, therefore, directly cause changes in the structure and consequently the function of the protein. Such an altered function of a protein can have devastating effects on the organism.

A large number of diseases caused by DNA mutations have been shown to be transmitted from one generation to another. In many instances, such mutations can be detected in the DNA of affected individuals by the use of cloned genes from the same gene of a part of the same gene from a normal individual. There are several techniques that can be utilized to the detection (diagnosis) of a mutation. The still most widely used method is called "Southern blotting". In this method, DNA from an affected individual is cut with specific restriction endonuclease enzymes into a number of specific size fragments that are then transferred to a filter paper. The fragments from a specific gene can then be visualized by a cloned radioactive fragment from the normal gene that specifically binds to the fragments of the same gene in the affected individual. Depending on the case, this analysis procedure can allow the detection of mutations involving single base changes or deletions or insertions of large DNA segments.

Another procedure for detecting genetic mutations involves amplification of a specific, possibly mutated, gene region with the use of the so-called polymerase chain reaction (PCR). In this method which requires the use of two synthetic oligonucleotides containing sequences from the region around the mutation, one can generate large enough quantities of a desired gene segment that can be further analyzed with a number of methods. This procedure has been successfully applied to examine DNA from only a few cells.

With the currently available gene technology it is possible to define in detail specific mutations in a large number of genetic diseases. This has led to the development of new DNA tests for prenatal diagnosis of serious genetic diseases or for finding out which individuals are carriers for a defective gene.

To date, there are several acquired and genetic diseases that involve changes in the structure and function of basement membranes. Accordingly, probes for the identification of changes in basement membrane genes or metabolism can be an important diagnostic tool to determine the existence of absence of such disease. Diabetes mellitus is a typical acquired disease where the basement membranes of small blood vessels become abnormally thick in a process that is known as microangiopathy. These changes, in turn, lead to the occlusion of small blood vessels and account for most of the late complications of diabetes such as kidney failure, neuropathy, necrosis of extremities and heart attacks. Several genetic basement membrane diseases affect kidney and skin. For example, polycystic kidney disease, the congenital nephrotic syndrome, and Alport's syndrome involve mutated genes that lead to malfunction of the basement membrane primarily in the kidney. However, the specific genes affected are, thus far, unknown. Also, skin blister diseases such as bullous pemphigoid and epidermolysis bullosa are characterized by basement membrane changes. In addition, there have been suggestions that alterations in basement membranes can play a significant role in the development of more complex multifactor diseases such as atherosclerosis and arteriosclerosis.

The present invention may be of significance for the diagnosis of basement membrane disorders but, in particular, the Alport's syndrome. This disease that is characterized by leaking of red blood corpuscles into urine (hematuria), ocular lesions and hearing loss is thought to be caused by a structural defect in the basement membrane. The defective gene causing the classical type of the disease has been localized to a specific region of the long arm of chromosome X, using so-called anonymous chromosome DNA markers (Atkin, et al., Am.J.Hum.Genet., 42, 249-255, 1988; Flinter, et al., Genomics, 4, 335-338, 1989). The actual gene is unknown, but Kleppel, et al. (J.Clin.Invest., 80, 263-266, 1987) showed evidence for an abnormal or even lack of a type IV collagen like α chain(s) in the renal basement membrane of patients with Alport's syndrome. However, it is obvious that the defective genes cannot be the genes for the human α1(IV) and α2(IV) chains since they have been mapped to chromosome 13 and no basement membrane component genes have so far been localized to chromosome X. In the applicants' recent work, however, the gene for the human α5(IV) chain was localized to the region on chromosome X where the Alport's syndrome gene is expected to be. Accordingly, since applicants have isolated a new type IV collagen chain and localized its gene to the locus of Alport's syndrome, it is possible that this novel gene is involved in the generation of the disease.

DETAILED DESCRIPTION OF THE INVENTION

The applicants have discovered a novel polypeptide chain that is a distinct gene product. This chain has a significant amino acid sequence homology with the already sequenced human α1 and α2 chains of basement membrane (type IV) collagen, as well as with the partially characterized α3(IV) and α4(IV) chains of the same collagen type. The new polypeptide chain that has been termed α5(IV), was discovered by the isolation and nucleotide sequencing of cDNA clones. Having previously isolated and sequenced cDNA clones coding for the entire human α1(IV) and α2(IV) chains, the applicants initiated work aiming at the isolation of the cDNA clones coding for other potential component chains of type IV collagen. The strategy for the work was to make use of the fact that a certain small region of the NC-domain of human and mouse α1(IV) and α2(IV) chains and that of an evolutionarily distant Drosophila type IV collagen α chain has 100% identical amino acid sequences. Based on this observation, it could be hypothesized that this sequence that has been conserved during evolution from Drosophila to man is essential for the structural organization of the NC-domains. Therefore, a similar sequence could expect to be present in all other related type IV collagen α chains, i.e. α3(IV), α4(IV) and other potential type IV collagen α chains.

The region in question consists of five amino acid residues with the sequence —Cys—Gln—Val—Cys—Met—and it is located very close to the carboxy terminal end of the NC-domain. Knowing this sequence, applicants could determine the corresponding DNA coding sequence in any gene coding for such an amino acid sequence based on the genetic code. In this case, the amino acids Cys, Gln, Val, and Met are encoded by nucleotide triplets with the sequences TG(TC), CA(AG), GT(ACGT), and ATG, respectively. The nucleotides shown in parenthesis mean that each of those indicated can be used alternatively as the third nucleotide in the triplet codon. This is called degeneration of the genetic code. As a result, in order to make an oligonucleotide that codes the sequence -Cys-Gln-Val-Cys--Met- one has to take into account all the possible nucleotide alternatives in the gene that in this case are a total of 32 different oligonucleotides. Accordingly, an oligonucleotide mixture containing 32 permutations was designed with the nucleotide sequence combination: TG(TC)—CA(AG)—GT(ACGT)—TG(TC)—ATG. These oligonucleotides were synthesized in a DNA synthesizer (Applied Biosystems, Inc., Foster City, Calif.) so that all 32 sequence possibilities were present in equimolar amounts.

The oligonucleotide mixture DNA was purified and then tagged at the end of the molecules with radioactively labeled phosphorus molecules and then used to screen a cDNA library for the presence of the cDNA clones containing some of the sequence or a sequence combination of the probe. Applicants chose a human placenta cDNA library because placental tissue contains a lot of basement membranes that are actively synthesized and it was known that such a library is rich in clones coding for the α1(IV) and α2(IV) chains of type IV collagen. Therefore, applicants presumed that the library would contain some clones for other type IV collagen chains, if such chains exist, at all. The cDNA library contained double stranded cDNA clones that were cloned into a λphage vector (λgt11) and the titer of this library was $10^9$ plaque forming units per ml. A small sample of this library containing a total of 360,000 clones was infected to *E.coli* bacteria for a short period after which the bacteria that had taken up the λphage DNA were plated on 12 agar plates, containing ampicillin, with such density that, on the average, each plaque growing from a bacterial clone was separated from the surrounding ones. Following an overnight incubation at 37° C., bacteria plaques on the plates were transferred to duplicate nitrocellulose filters by placing them on top of the agar plates. The orientation of the filters with respect to the agar plates was marked for later identification when picking plaques of interest.

Once the duplicate filter copies had been made from each plate, the walls of the bacteria were lysed and the DNA in the bacterial plaques was then bound to the filter with standard techniques. The DNA from the bacteria plaques was present on the filters as small, fairly well separated dots, each dot usually being derived from a single parent bacterium that contained a single cDNA clone, in addition to its own genomic DNA. The majority of the dots should contain amplified DNA from a single cDNA clone present in the original cDNA library.

In order to find bacteria containing cDNA clones with a nucleotide sequence coding for the Cys-Gln-Val-Cys-Met sequence that the applicants were interested in, the filters were first hybridized with the labeled oligonucleotide mixture. During the hybridization procedure the synthetic oligonucleotide probes should bind to complementary DNA from double-stranded DNA containing this sequence and leave a radioactive spot on the filter after all nonspecific binding has been washed away. This radioactive spot could then be localized with autoradiography. In this regard, the filters were placed on X-ray films causing exposure of the films at the site of radioactive spots Any exposed dot, referred to as a positive screening signal, could then be traced back to a certain plague on the original bacterial master plate. This particular plaque should contain bacteria in which there was a λphage clone coding for the Cys-Gln-Val-Cys-Met amino acid sequence.

In this regard, the applicants found only 720 positive signals on the films, meaning that out of the 360,000 plaques that were screened, only 720 contained clones for this sequence. Since the applicants assumed that a large portion of these signals was due to sequences from clones coding for the α1(IV) and α2(IV) chains that have already been completely cloned, they hybridized the filters with probes for these chains and could find 40 signals that did not hybridize. Accordingly, these 40 clones should code for something else than the α1(IV) and α2(IV) chains. The 40 plaques were then picked, replated on agar and grown, transferred to filters and hybridized with the oligonucleotide mixture probe. The inventors obtained eight strong positive signals. The bacteria containing the λphage with these eight cDNA clones were then grown in mass cultures for large scale preparation and subcloned into so-called sequencing vectors for further identification. Only two of those (MD6 and M19) were shown to contain a DNA sequence coding for a type IV collagen like protein and these clones, that together covered 2,500 bp, were then used to isolate longer cDNA clones. This yielded one clone (PL31) of 2,000 bp that added about 950 bp to the nucleotide sequence determined by the MD6 and M19 cDNA clones. Altogether, the three clones covered a total of 3,500 bp (FIG. 1).

A modified Northern hybridization procedure was then carried out to determine the size of the mRNA coding for the protein involved. This was done by labeling one of the cDNA clones (MD-6) with $^{32}P$ and hybridizing the probe to kidney RNA that had been size fractionated on an electrophoresed agarose gel and transferred to nitrocellulose. This analysis, in turn, demonstrated that the complete mRNA had the size of about 6,500 bp and, therefore, the clones code for about 50% of the entire mRNA. The sizes of the mRNAs for the human α1(IV) and α2(IV) chains are also of the same size, so that the polypeptide chain encoded by the new clones studied is most likely of a similar size.

Figure 2A:
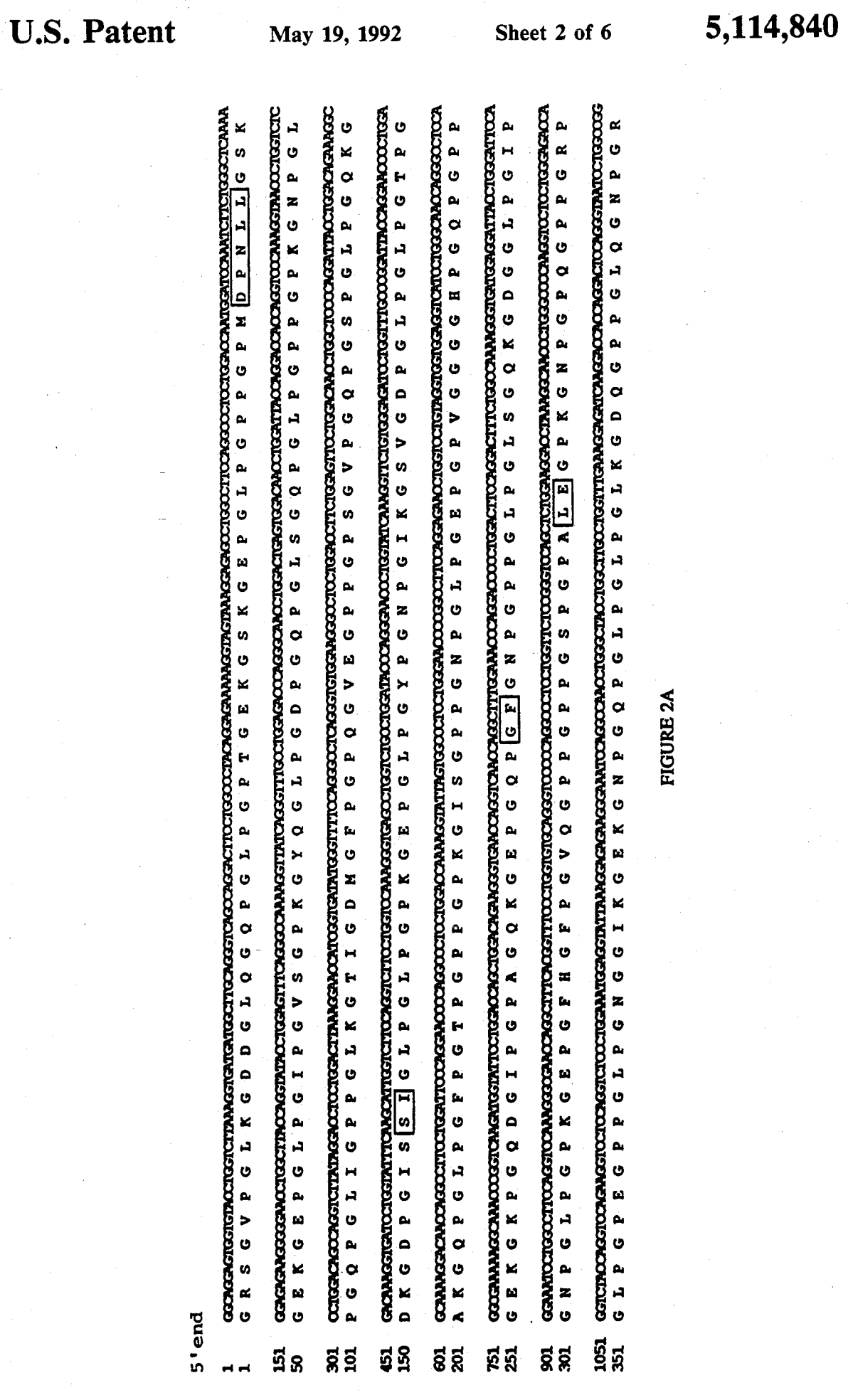
Figure 2B:
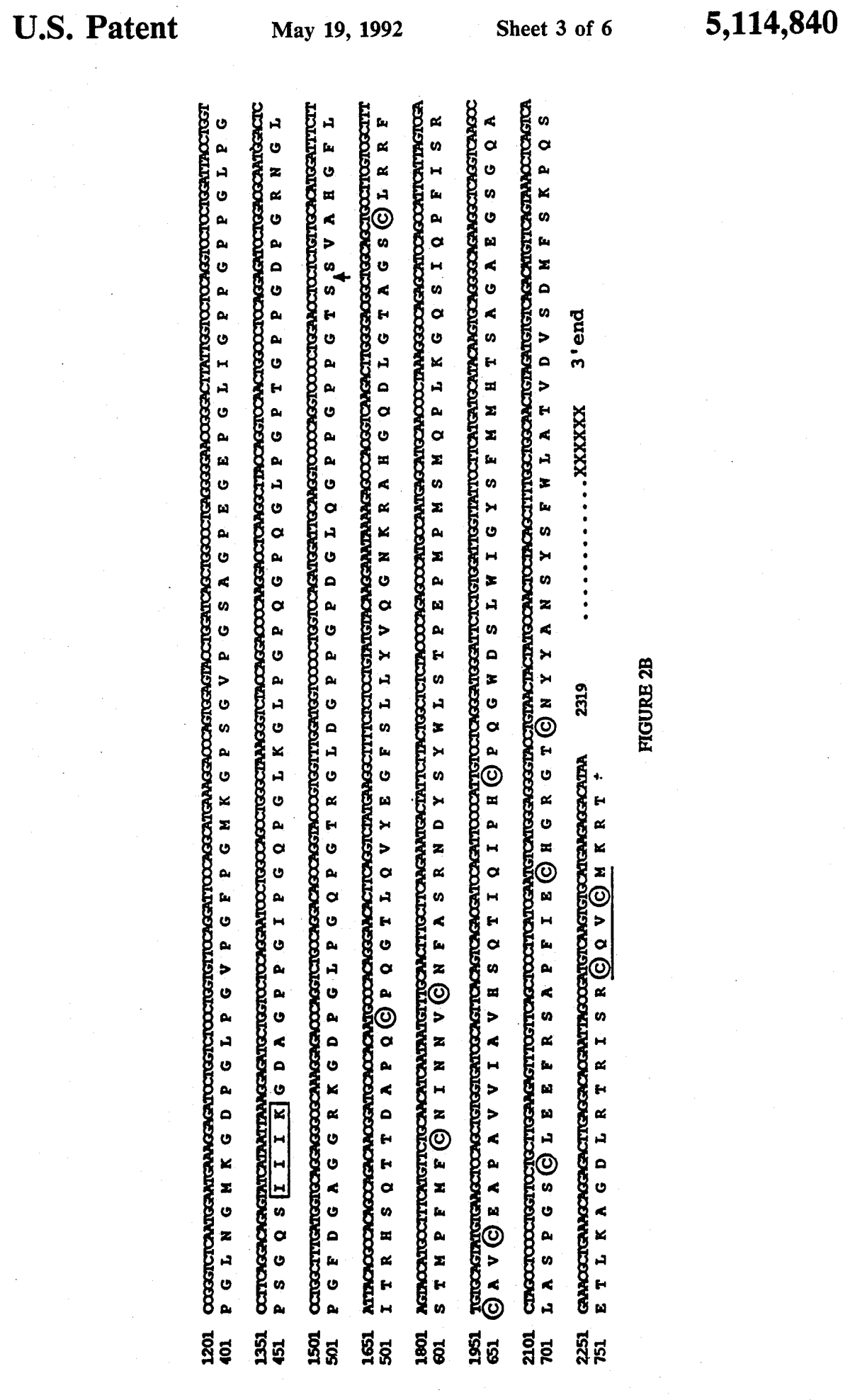

The entire sequence of the nucleotide sequence contained in the three overlapping cDNA clones was determined in order to find out which protein sequences they might encode. For that purpose, cDNA clone inserts were subcloned into M13 sequencing vectors and sequenced with the standard chain termination reaction. For the sequencing, the inventors used first the "universal" primer that provided about 250-300 bp of nucleotide sequence from the ends of the inserts. The rest of the sequence was obtained with the "primer walk" procedure where synthetic oligonucleotides were used. The sequence of these oligonucleotides was always designed based on the sequence obtained in the former round. By this method, the inventors determined the complete sequence of the cDNA clones that codes for amino acid sequence in the corresponding protein, or a total of 2,319 bp including the so-called stop codon (FIG. 2). The sequence revealed the cDNA clones contained an open reading frame at the 5' end of 2,316 bp coding for 772 amino acids followed by the TAA stop codon and about 1,200 bp of a so-called 3' end untranslated sequence that is not translated into an amino acid sequence. The 3' untranslated region was not sequenced to completion (FIG. 2). Since the clones were identified with an oligonucleotide coding for the amino acid sequence Cys-Gln-Val-Cys-Met the clones should also contain a coding sequence for it. This was indeed the case since nucleotides no. 288-2307 from the 5' end had the sequence TGTCAAGTGTGCATG that codes for Cys-Gln-Val-Cys-Met.

Figure 3A:
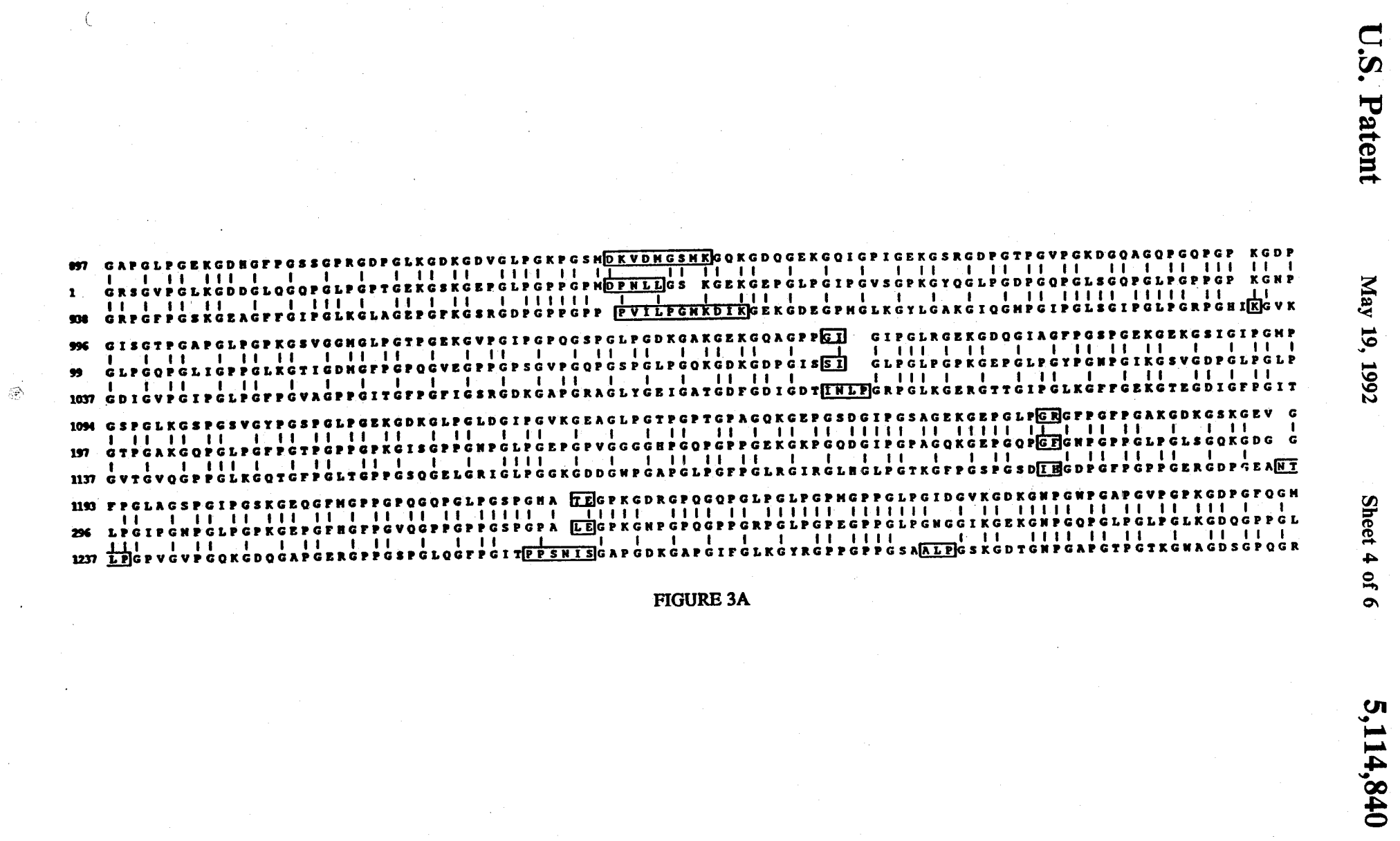
Figure 3B:
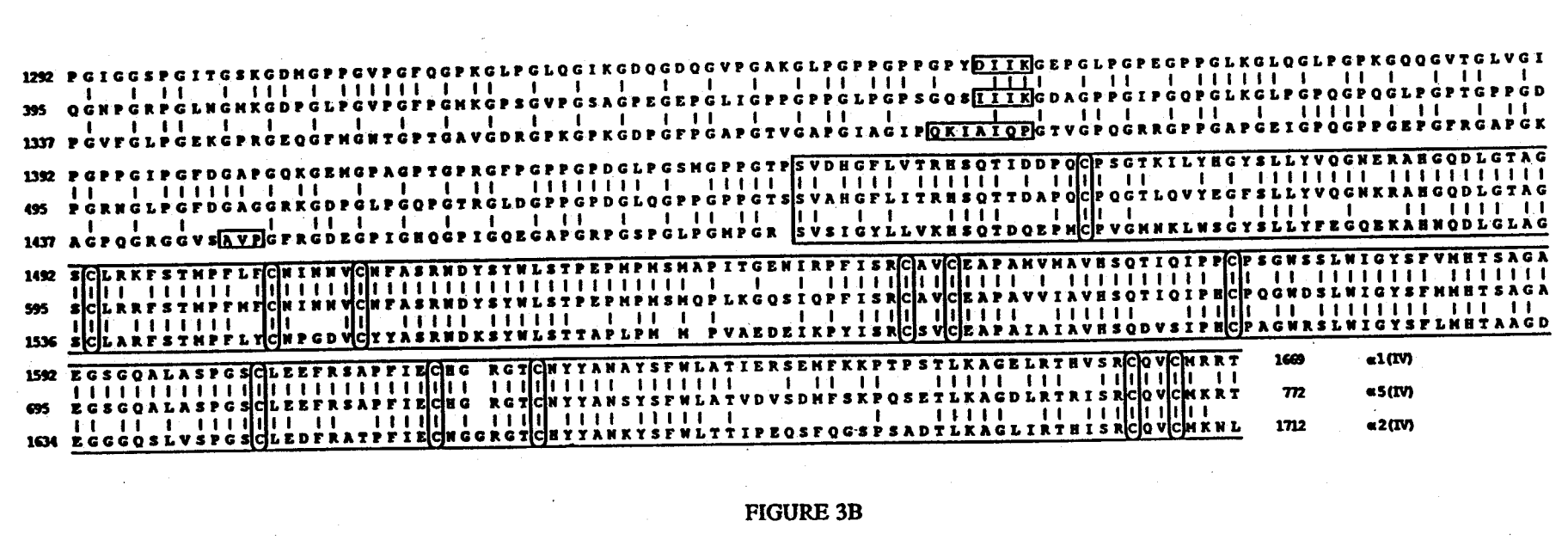

Having identified the Cys-Gln-Val-Cys-Met coding sequence, a sequence present in all known type IV collagen α chains characterized before, it was of interest to know whether or not the rest of the predicted amino acid sequence resembled the known α chains of type IV collagen in any way. Interestingly, this turned out to be the case. The amino acid sequence derived from the new cDNA clones could easily be aligned with the sequences of the human α1(IV) and α2(IV) chains (FIG. 3). It was intriguing to observe that the new chain contains a complete carboxy terminal domain that resembles extensively the NC-domain of the α1(IV) and α2(IV) chains, indicating that the novel chain described in this invention belongs to the collagen IV family. The homology includes an almost exactly equal length NC-domain with all the cysteine residues conserved. The sequence identity in the NC-domain with that of the human α1(IV) chain is 83% and with that of the α2(IV) chain considerably less or 64%. In the region of the chain containing collagenous sequences with the typical Gly-X-Y repeat sequences, the new chain also showed a higher degree of identity with the α1(IV) than the α2-(IV) chain. The inventors also compared the sequence of the new chain with the short sequences already known for the α3(V) and α4(IV) chains. This comparison demonstrated that the novel chain of the invention was also different from those two chains (FIG. 4). The novel chain has only 43% homology with the α3(IV) chain and as little as 18% homology with the α4(IV) chain.

Taken together (i.e. FIGS. 1 and 2), the cloned cDNAs of the present invention clearly demonstrate that they contain sequences for a previously unknown gene product coding for a novel polypeptide chain that belongs to the type IV collagen family. Since it is a distinct gene product different from the α1(IV), α2(IV), α3(IV), and α4(IV) chains of the type IV collagen, the inventors refer to this novel chain as the α5(IV) chain of type IV collagen.

Furthermore, as a result of the isolation and partial characterization of the nucleotide sequence, the present invention is also directed to the use of the nucleotide sequence and/or the cDNA clones thereof, for tests that can be used to determine genetic or acquired disorders of basement membranes using α5(IV) chain DNA probes specific for the identified nucleotide sequence (or DNA fragments thereof) or antibodies to the nucleotide sequence or DNA parts thereof. More particularly, such uses include a method for identifying the gene coding for the α5(IV) chain of human type IV collagen which comprises hybridizing a cDNA which codes for part of the α5(IV) polypeptide chain of human type (IV) collagen with human genomic DNA, and determining whether the cDNA anneals to the genomic DNA. Along this line, the present invention can also be utilized in the form of a method for identifying the messenger RNA transcript of a gene coding for the α5(IV) chain of human type IV collagen by a very similar process. In this regard, a method for identifying the mRNA transcript of the gene coding for the α5(IV) chain for human type IV collagen comprises the steps of hydrizing a cDNA clone which codes for the human α5(IV) polypeptide chain of human type IV collagen with a mRNA transcript, and determining whether the cDNA anneals to the messenger RNA transcript.

Furthermore, the present invention relates to the use of gene fragments generated through amplification from human genomic or cloned DNA for detection and analysis of the gene, such as in the detection of mutations. A method for amplifying a nucleotide sequence specific for the human gene for the α5(IV) chain of the type IV collagen from biological samples containing human genomic DNA using the synthetic oligonucleotide primers of the present invention which contain either a nucleotide sequence from the gene or from the cDNAs encoding axions of the genes, such a method would comprise the steps of synthesizing the oligonucleotides containing the nucleotide sequence wherein the nucleotide sequence are specific for the gene for the α5(IV) chain of human type IV collagen, allowing the oligonucleotides to anneal to the specific sequences in the sample containing the human genomic DNA, synthesizing a copy of each strand of the DNA by polymerase chain reaction, and denaturing the sample to separate the DNA strands from each other.

In addition, as elaborated above, the present invention also relates to the potential use of the nucleotide sequence synthesized above for cloning purposes. Other alternative embodiments for new and unique uses of nucleotide sequences, the cDNA clones, the unique α5(IV) polypeptide chain of human type IV collagen, etc. may be utilized by procedures that are well known in the art.

The following examples further illustrate the specific embodiments of the present invention.

EXAMPLE 1

Isolation and Identification of cDNA clones coding for the human α5(IV) chain

A human placenta cDNA library cloned into the EcoRI site of λgt11 phage was used for screening. A sample of the library containing a total of 360,000 plague forming units (pfu) was used to infect E.coli cells that were then plated on agar plates. For each plate, a sample of 30,000 pfu was infected to 300 μl E.coli Y 1090 plating bacteria (in 20 mM MgSO$_4$) at 37° C. for 20 minutes and plated in 7 ml of top-agar (1% tryptone, 0.8% NaCl, 1.4% LMP-agar) on agar plates containing 1% tryptone, 0.5% yeast extract, 0.5% NaCl and 100 μg/ml ampicillin. The λphage were grown at 37° C. overnight. Duplicate nitrocellulose filters were made by allowing them to stand on the plate for 1 and 2 minutes following 5 minutes denaturation in 0.5 M NaOH, 1.5 M NaCl; neutralizing in 1 M Tris (Tris[hyroxymethyl]aminomethane), pH 8.0, 1.5 M NaCl for 5 minutes and balancing to 2xSSC (1xSSC is 0.15 M NaCl, 0.015 M sodium citrate, pH 7.0) before air drying and baking at 80° C. for 2 hours.

For hybridization, the nitrocellulose filters were balanced in 5xSSC and then washed in 3xSSC, 0.1% SDS (sodium dodecyl sulphate) at 65° C. overnight. Prehybridization was performed in 6xSSC, 5xDenhardts, 0.5% SDS, 100 μg/ml denatured salmon sperm DNA, 0.05% Na pyrophosphate (50xDenhardts is 1% Ficoll, 1% polyvinylpyrrolidone, 1% BSA) for 2 hours at 37° C. and hybridized with labeled oligonucleotide mixture in 6xSSC, 5xDenhardts, 250 μg/ml denatured salmon sperm DNA, 0.05% Na pyrophosphate overnight at 37° C.

The amino acid sequence Cys-Gln-Val-Cys-Met is the most carboxy-terminal (and therefore in the corresponding cDNA the most 3') consensus sequence of the NC-domains of the type IV collagen in all known α chains in all species studied thus far. Therefore, this sequence was used as basis for the design of an oligonucleotide probe mixture. This sequence also has the smallest amount of degeneration of the genetic code (see above), giving 32 different alternatives in a 15-mer oligonucleotide. An oligonucleotide mixture TG(TC)CA(AG)-GT(ACGT)-TG(TC)-ATG coding for this amino acid sequence was synthesized with a DNA synthesizer from Applied Biosystems, Inc. For the preparation of probe 500 ng of the oligonucleotide mixture was end-labeled with 100 μCi adenosine 5'[−$^{32}$P]triphosphate (in 10 μl; Amersham, PB 10168) in 20 mM MgCl$_2$, 200 mM Tris, pH 7.6, 40 mM β-mercaptoethanol with 1U of T4-polynucleotide kinase in a 40 μl reaction mixture at 37° C. Differing with the alternative oligonucleotides, Tm=39.6−50.5° C. Following labeling, the DNA was separated from unincorporated label by spinning down through a Spehadex G-50 column.

The duplicate filters were washed with 6xSSC, 0.05% Na pyrophosphate once at room temperature, twice 10 minutes at 37° C. and at least twice for 10 minutes at 42° C. Autoradiography was performed at −70° C. for two to four days (DuPont Cronex).

Before rehybridization of the filters with the α1(IV) and α2(IV) specific cDNA probes, the library filters were washed first with water at 65 C and 80° C. to remove all probe bound to the filters during the first hybridization and then balanced to 10xSSC. Nick translation labeling of the cDNA inserts with deoxycytidine 5'−[α−$^{32}$P]triphosphate (Amersham, PB 10205) was carried out using a Promega Biotec nick translation kit according to the manufacturer's instructions. The filters were prehybridized for 2 hours and then hybridized with the labeled cDNA probes overnight at 65° C. in 5xSSC containing 5xDenhardts, 0.1% SDS, 50 μg/ml denatured salmon sperm DNA. Before autoradiography, the filters were washed first in 2xSSC, 0.1% SDS at room temperature and then at 65° C. with several changes in a washing solution 0.2xSSC, 0.1% SDS. Autoradiography was done at −70° C. overnight.

Clones showing duplicate positive signal for the oligonucleotide mixture and negative for the cDNA clones were picked and rescreened with the oligonucleotide mixture until pure plaques were isolated. Phage were grown in large quantities and isolated as pure λphage DNA with a rapid method containing DNAse I and RNAse A treatments of the lysed growth medium followed by PEG precipitation, proteinase K digestion, phenol and chloroform extractions as well as ethanol precipitations. λphage DNA of the clones was digested with EcoRI restriction endonuclease and electrophoresed in a 1% agarose gel containing ethidium bromide to separate the cDNA inserts from the gt11 vector and to determine their sizes. The DNA was transferred from the gel to a nitrocellulosefilter by Southern blotting and hybridized with the oligonucleotide mixture. cDNA inserts positive for the oligonucleotides were isolated and subcloned to the M13 vector for sequencing and pUC18 for producing quantities required for rescreening the library for longer clones. A partial restriction map of the cDNA clones is shown in FIG. 1.

EXAMPLE 2

Nucleotide sequencing of cDNA clones

The cDNA clone inserts were subcloned directly into the EcoRI site of M13mp18 vector so that they were inserted in both orientations. These recombinants were then sequenced first from both ends to determine whether they contained type IV collagen like sequences. Nucleotide sequencing was carried out with the Sanger dideoxy nucleotide sequencing method using Sequenase (United States Biochemical Corporation) and deoxyadenosine $5'(\alpha-[^{35}S]$thio)triphosphate (Amersham, SJ1304) according to the manufacturer's instructions. Both the "universal primer" and sequence specific oligonucleotides were used as primers.

Clone MD6 was shown to have a Gly-X-Y repeat coding sequence typical for collagenous proteins at one end and a typical NC-domain coding sequence at the other end. However, the sequences were clearly different from those of the human $\alpha1$(IV) and $\alpha2$(IV) chains and also distinct from known parts of $\alpha3$(IV) and $\alpha4$(IV) chain sequences. Therefore, this clone was used to screen for more cDNA clones that would provide a longer coding sequence for this previously unknown $\alpha$ chain, termed $\alpha5$(IV). A new clone, PL31, was found and sequenced as before. Together with the previous clones, the three clones contained a total of 3490 bp the translated sequence of which along with the predicted amino acid sequence is shown in FIG. 1.

EXAMPLE 3

Northern Analysis

Total RNA was isolated from cells or tissue samples using single-step method by acid guanidinium thiocyanatephenol-chloroform extraction (Chomczynski & Sacchi (1987) Anal. Biochem. 162, 156–159). Samples of 10 μg total RNA in 20 mM MOPS (3-[N-morfolino]-propanesulfonic acid), pH 7.0, 5 mM sodium acetate, 0.5 mM EDTA-$Na_2$, 2.2 M formaldehyde, 50% formamide in 20 μl were denatured for 15 minutes at 65° C. and 2 μl dye solution (50% glycerol, 1 mM EDTA, 0.4% bromphenolblue, 0.4% xylencyanol FF) was added. Samples were loaded to 1% agarose gel in 20 mM MOPS, pH 7.0, 5mM sodium acetate, 0.5 mM EDTA-$Na_2$, 2.2 M formaldehyde and electrophoresed. Gel slide containing Hind III fragmented phage molecular weight standard (20 μg) and duplicate RNA samples was stained with 0.5 μg/ml ethidium bromide for 30 minutes, washed three times 30 minutes with water and photographed.

Both stained and unstained pieces of gel were treated 45 minutes with 10 mM NaCl, 50 mM NaOH, 45 minutes with 0.1 M Tris, pH 7.5, and 30–60 minutes with 10xSSC before blotting to NC-filter overnight. Northern hybridization was done in 50% formamide, 5xSSC, 0.1% SDS, 5xDenhardts, 200 μg/ml denatured salmon sperm DNA at 42° C. with 2 hours prehybridization and hybridizing with nick translated cDNA insert for 2 days. NC-filters were washed with 2xSSC, 0.1% SDS first at RT and then several washings at 65° C. Autoradiography was performed at −70° C. for up to two weeks.

Northern analysis with cDNA insert MD6 showed mRNA size 6.5kb. As to confirm this, the same filter was hybridized with $\alpha1$(IV) cDNA clone and the mRNAs detected were of a similar size.

EXAMPLE 4

Comparison of the amino acid sequence of the novel $\alpha5$(IV) chain with that of the $\alpha1$(IV), $\alpha2$(IV) and known parts of $\alpha3$(IV) and $\alpha4$(IV) chains Comparison of the human $\alpha5$(IV) chain to human $\alpha1$(IV) and $\alpha2$(IV) chains is shown in FIG. 3. The amino acid sequences are aligned according to (Hostikka & Tryggvason, J.Biol.Chem., 263, 19488–19493, 1988) showing maximal identity with conserved elements coinciding and gaps have been left when a deletion from one chain or insertion to another is proposed. FIG. 4 shows comparison of junction sequences with of $\alpha3$(IV) and $\alpha4$(IV) chains.

The invention has been described with reference to the preferred embodiments. Obviously, modifications and alterations will occur to others upon reading and understanding the preceding detailed description. It is intended that all such alterations and modifications insofar as they come within the scope of the appended claims or the equivalents thereof.

Having thus described the preferred embodiment, the invention is now claimed to be:

1. A process for isolating cDNA clones which code for part of the $\alpha5$(IV) polypeptide chain of human type IV collagen comprising the steps of:
  a) synthesizing the oligonucleotide sequences that code for the amino acid sequence —Cys—Gln—Val—Cys—Met—;
  b) screening a cDNA library containing clones coding for human type IV collagen with said oligonucleotide sequences in order to isolate those cDNA clones coding for type IV collagen containing the synthesized oligonucleotide sequences;
  c) cloning the isolated cDNA clones coding for human type IV collagen, containing the synthesized oligonucleotide sequences into a vector and inserting the vector into a bacterial host;
  d) duplicating and marking said bacteria hosts for reference;
  e) lysing the original bacteria hosts and binding the DNA contained therein to a filter;
  f) hybridizing the DNA bound on the filter with oligonucleotide sequences that code for the amino acid sequence —Cys—Gln—Val—Cys—Met—;
  g) hybridizing the positively hybridized DNA with cDNA clones coding for $\alpha1$(IV) and $\alpha2$(IV) polypeptide chains of type IV collagen and determining which of those previously positively hybridized collagen DNA did not hybridize with the cDNA clones coding for the $\alpha1$(IV) and $\alpha2$(IV) polypeptides;
  h) replating the duplicate bacterial hosts of those cDNA clones which positively hybridized collagen DNA but did not hybridize with the clones coding for the α1(IV) and α2(IV) polypeptides;

i) lysing the duplicated bacterial hosts and separating the vector from the cDNA inserts;

j) subcloning the cDNA inserts into a second vector for sequencing; and, k) sequencing the cDNA inserts thereby identifying the isolated cDNA clones which encode for part of the α5(IV) polypeptide chain of human type I collagen.

2. The process of claim 1, wherein said oligonucleotide sequences that code for the amino acid sequence —Cys—Gln—Val—Cys—Met—comprise the 32 permutations designed with the nucleotide sequence combination:

TG(TC)—CA(AG)—GT(ACGT)—TG(TC)—ATG.

3. The process of claim 1, wherein said cDNA library containing clones coding for human type IV collagen comprises a human placenta cDNA library.

4. The process of claim 1, wherein said vector cloned with the isolated cDNA clones coding for human type IV collagen containing the synthesized oligonucleotide sequences comprises a λphage vector ( λgt 11).

5. The process of claim 1, wherein said bacterial host comprises E.coli.

6. The process of claim 1, wherein said second vector for subcloning the cDNA inserts into for sequencing is M13.

7. The process of claim 1, wherein said second vector for subcloning the cDNA inserts into for sequencing is pUC18.

8. The cDNA clones which code for part of the α5-(IV) polypeptide chain of human type IV collagen isolated by the process of claim 1.

9. The cDNAs which code for part of the α5(IV) polypeptide chain of human type IV collagen identified in FIG. 1.

10. A cDNA which codes for the part of the c5(IV) polypeptide chain of human type IV collagen comprising the cDNA clone identified as PL31.

11. A cDNA which codes for the part of the α5(IV) polypeptide chain of human type IV collagen comprising the cDNA clone identified as MD6.

12. A cDNA which codes for the part of the α5(IV) polypeptide chain of human type IV collagen comprising the cDNA clone identified as M19.

13. The cDNA of claim 10, wherein said cDNA identified as PL31is comprised of 1,980 bp.

14. The cDNA of claim 11, wherein said cDNA identified as MD6 is comprised of 2,535 bp.

15. The cDNA of claim 12, wherein said cDNA identified as M19 is comprised of 1,060 bp.

16. A process for identifying the nucleotide sequence for part of the α5(IV) polypeptide chain of type IV collagen comprising the steps of:

a) synthesizing the oligonucleotide sequences that code for the amino acid sequence —Cys—Gln—Val—Cys—Met—;

b) screening a cDNA library containing clones coding for human type IV collagen with said oligonucleotide sequences in order to isolate those cDNA clones coding for type IV collagen containing the synthesized oligonucleotide sequences;

c) cloning the isolated cDNA clones coding for human type IV collagen containing the synthesized oligonucleotide sequences into a vector and inserting the vector into a bacterial host;

d) duplicating and marking said bacteria hosts for reference;

e) lysing the original bacteria hosts and binding the DNA contained therein to a filter;

f) hybridizing the DNA bound on the filter with oligonucleotide sequences that code for the amino acid sequence —Cys—Gln—Val—Cys—Met—;

g) hybridizing the positively hybridized DNA with cDNA clones coding for α1(IV) and α2(IV) polypeptide chains of type IV collagen and determining which of those previously positively hybridized collagen DNA did not hybridize with the cDNA clones coding for the α1(IV) and α2(IV) polypeptides;

h) replating the duplicate bacterial hosts of those cDNA clones which positively hybridized collagen DNA but did not hybridize with the clones coding for the α1(IV) and α2(IV) polypeptides;

i) lysing the duplicated bacterial hosts and separating the vector from the cDNA inserts;

j) subcloning the cDNA inserts into a second vector for sequencing;

k) sequencing the cDNA inserts for identification; and, l) identifying the nucleotide sequence for part of the α5(IV) polypeptide chain of type IV collagen by determining the nucleotide sequence of the overlapping cDNA clones.

17. The nucleotide sequence for the part of the α5-(IV) polypeptide chain of human type IV collagen identified by the process of claim 16.

18. An isolated human DNA sequence which codes for part of the α5(IV) of human type IV collagen as shown in FIG. 2.

19. An isolated human DNA sequence which codes for part of the α5(IV) chain of human type IV collagen comprising cDNA having at its 5' end a sequence coding for a collagen domain sequence Gly-Arg-Ser-Gly, and at its 3' end a sequence coding for a carboxy terminal noncollagenous-domain and a 3' noncoding region.

20. An isolated human DNA sequence which codes for part of the α5(IV) chain of human type IV collagen comprising a DNA sequence which has the restriction endonuclease map of the three cloned cDNAs shown in FIG. 1.

21. The isolated human DNA sequence of claim 20, wherein the three cDNAs are PL31, MD6 and M19.

22. A cloning vector comprising the DNA sequence of claim 17.

23. A cloning vector comprising the DNA sequence of claim 18.

24. A cloning vector comprising the DNA sequence of claim 20.

25. The cloning vector of claim 22, further comprising a vector selected from the group consisting of M13 and pUC18.

26. The cloning vector of claim 23, further comprising a vector selected from the group consisting of M13 and pUC18.

27. The cloning vector of claim 24, further comprising a vector selected from the group consisting of M13 and pUC18.

* * * * *